US00PP09005P

United States Patent [19]

Chang

[11] Patent Number: Plant 9,005

[45] Date of Patent: Dec. 6, 1994

[54] MANGO TREE FP1

[76] Inventor: Min H. Chang, 1,2 Lin, Ne-Won Village, Fan-Ru Shiang, Chia-Yi Hsien, Taiwan, Prov. of China

[21] Appl. No.: 913,797

[22] Filed: Jul. 16, 1992

[51] Int. Cl.[5] ..... A01H 5/00
[52] U.S. Cl. ..... Plt./33.1
[58] Field of Search ..... Plt. 33.1

*Primary Examiner*—James R. Feyrer
*Assistant Examiner*—E. F. McElwain
*Attorney, Agent, or Firm*—Jacobson, Price, Holman & Stern

[57] ABSTRACT

A mango tree "FP1" bearing fruit is disclosed. The fruit is distinguished from other mango varieties by its medium fruit size, high juice content, low fiber content, small core, good taste with high sugar content, low acidity, strong resistance to wind, anthracnose resistance, and good storage capacity.

2 Drawing Sheets

BACKGROUND OF THE INVENTION

A good yield "White" mango tree F1 was discovered by Mr. Min-Hsien, Chang, in Her-Lon Oil Factory at Min-Hsiung, Chia-Yi Hsien, Taiwan, in 1966. The fruit of the discovered mango tree F1 was characterized as having the same shape, flesh and flavor as that of "White", but its yield was much more abundant than that of "White". Mr. Chang found it was the first filial generation (F1) of a "White" mango tree variety and a common named local mango tree variety. He grafted a shoot from it to a two-shoot "Irwin" mango tree at the time. In 1969, some fruit of the first crop, about 1 to 2% of the terminal fruits on said shoot were the hybrid fruits of xenia by open pollination. The hybrid fruit was characterized as having the same coloration as that of "Irwin", but the shape, flesh and flavor remained the same as that of "White". Mr. Chang planted the hybrid fruits in the ground at that time. He smelled the leaves of the plants in order to determine whether the flavors were the same as the local mango variety. He used the young seedlings having the same flavor as the local mango variety. In 1976, he obtained a tree "FP1" of the new plants which was derived from the shoot of cultivar "F1", grafted onto "Irwin", which was crossed by open pollination resulting in the production of hybrid seeds and bore its first crop of fruit, which were attractive, medium size, high juice content, low fiber content, good taste with high sugar content (Brix 15), low acidity (0.19%), small core, strong resistance to wind, anthracnose resistance and good storage capacity.

The tree of the mango variety "FP1" of this invention has been repeatedly asexually reproduced by planting of the buds of "FP1" in the ground. Such asexual reproduction uniformly produces a fruit of the character described herein.

SUMMARY OF THE INVENTION

The invention is directed to a mango tree variety "FP1" which is the result of a hybrid cross of cultivars "F1" and "Irwin". The mango tree produces medium red fruit on a yellow ground color, and matured in May. "FP1"]is distinguished from other mango varieties by its medium fruit size, high juice content, low fiber content, small core, good taste with high sugar content, low acidity, strong resistance to wind, anthracnose, resistance and good storage capacity. The harvest date of the mango fruit is 90–110 days depending on the weather. The productivity is abundant in fruits of about 60 kg in a 6–8 year old tree. With respect to the duration of the fruit stored in the tree, the fruit will drop in a protective bag about three days after maturity. The fruit can be held under controlled storage conditions for about 15–30 days.

DETAILED DESCRIPTION OF THE INVENTION

Figure 1:
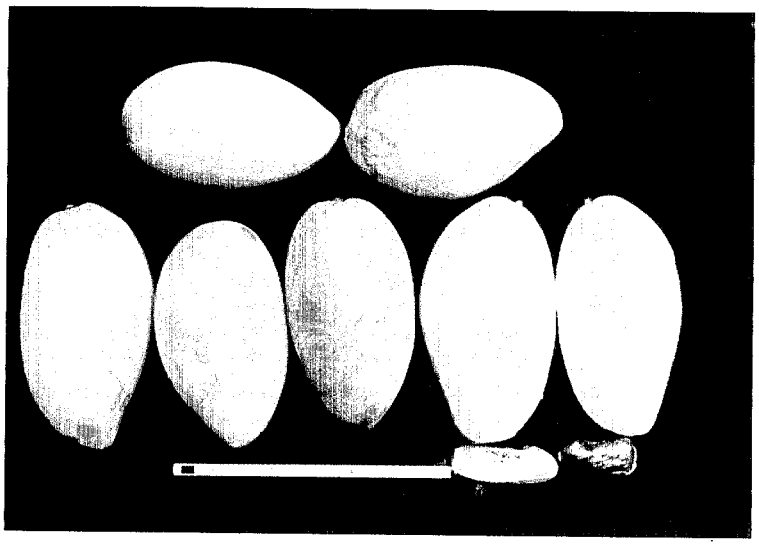
FIG. 1 is a photograph of fruit of "FP1".
Figure 2:
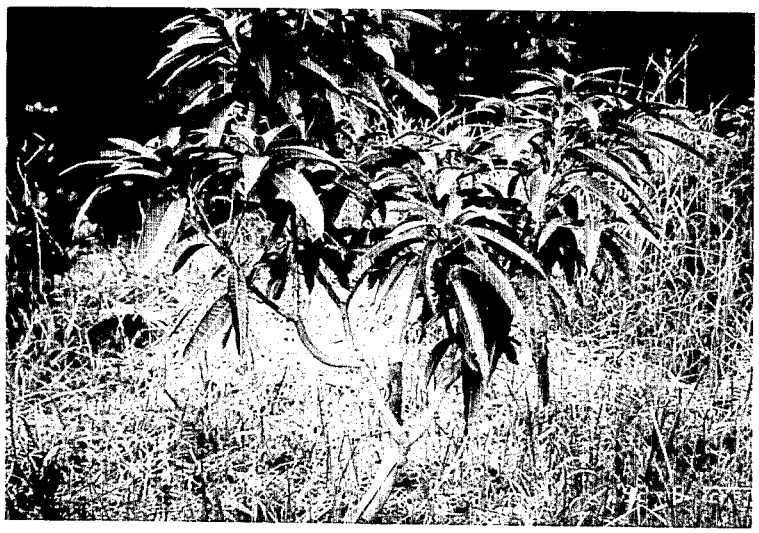
FIG. 2 is a photograph of the original tree of "FP1".
Figure 3:
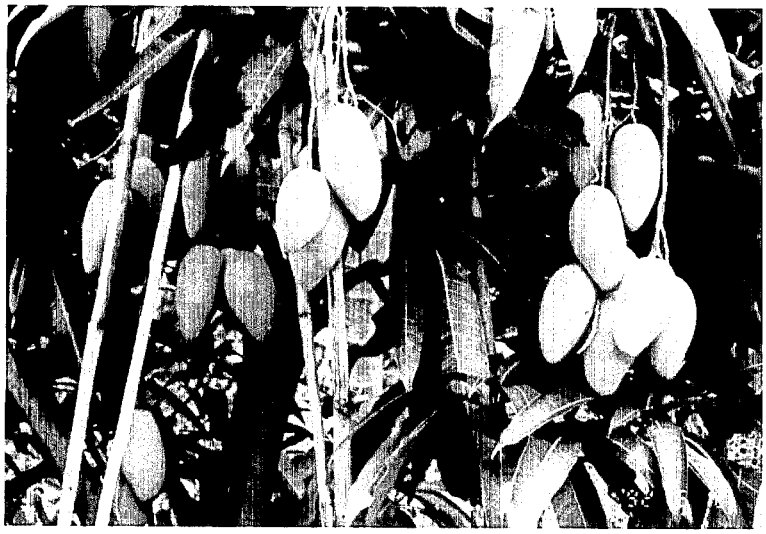
FIG. 3 is a photograph of the original tree of "FP1" bearing fruits.

The following is a description of the characteristics of the mango tree variety of this invention.

Tree:
- *Tree vigor.*—High. The terminal growth during the winter is 15 cm, and during the summer is 30 cm.
- *Tree size.*—Medium about 21 years old.
- *Tree type.*—Long oval.
- *Height.*—4.5 m.
- *Girth.*—14 m.
- *Maturity.*—In May.
- *Pollination.*—Open pollinated.
- *Location.*—Chia-Yi, Taiwan.
- *Pruning.*—Twice a year. The first time is in spring, any time at its bearing. The bent flower stalk without fruits and the slim twigs should be cut out for easy management. The second time is in summer, any time after the harvest. The drooped branches should be cut out for high productivity in the next season.
- *Bark.*—Smooth.
- *Petiolate.*—Tough, resistant to wind damage.
- *Bloom.*—Early, on December, full blooming on February.

Leaf:
- *Length.*—30.5 cm.
- *Width.*—6.5 cm.
- *Thickness.*—0.5 cm.
- *Color.*—Green near 143B.
- *Leaf type.*—Large, oval-lanceolate, personate verticillate.
- *Leaf surface.*—Glabrous and smooth.

*Petiole.*—6.5 cm in length.

*Extrapolated tree size.*—A chopped "Local Mango Variety" mango tree of 2 years old, about 1 m in height and about 1 cm in girth is the best.

Panicle:

*Inflorescence.*—Conic, axil and terminal, about 15–40 cm, normally having ramify 2 or 3 times and the last ramification has 3 flowers as an umbrella. Every inflorescence has 500–3,000 flowers. Each flower is about 0.5–0.8 cm.

*Calyx.*—5 pieces.

*Petal.*—5 pieces.

*Stamen.*—5 pieces, but normally only 1 or 2 stamen in full growth could disseminate pollen. And, the shape of a grain of the pollen is oval.

*Flower.*—Has the staminate flower and the gynandrous flower. The average of the gynandrous flower is 3–60%.

Fruit:

*Weight.*—553.8 g.

*Size.*—Axial diameter 159.3 mm. Transverse diameter 78.1 mm.

*Skin color.*—Red on a yellow ground.

*Flesh.*—Fine, gold, juicy, small amount.

*Aroma.*—Comparable to the local mango variety.

*Sweetness.*—High sugar content (Brix 15).

*Acid.*—Low acidity (0.19%).

*Thickness of skin.*—0.8–1.0 cm.

*Fruit count per pannicle.*—7–8 pieces.

*Storage.*—The fruit will drop in a protective bag about 3 days after maturity. The fruit can be held without any handling requirements for about 15–30 days.

*Susceptibilty to bruising.*—Not easy.

Core:

*Weight.*—43.8 g.

*Size.*—Axial diameter 142.6 mm, Transverse diameter 40.3 mm.

*Difficulty of separation.*—Easy.

*Fiber.*—Only a latter around the core.

Seed:

*Weight.*—21.3 g.

*Size.*—Axial diameter 74.4 mm. Transverse diameter 30.5 mm.

LIST OF COMPARISON BETWEEN F1, FP1 AND IRWIN

| NAME | F1 | FP1 |
|---|---|---|
| Leaf | Length: 29 cm<br>Width: 8.5 cm<br>Thickness: 0.5 mm | Length: 30.5 cm<br>Width: 6.5 cm<br>Thickness: 0.5 mm |

-continued

LIST OF COMPARISON BETWEEN F1, FP1 AND IRWIN

| | | |
|---|---|---|
| | Color: Dark green near G135B | Color: Green near 143B |
| Petiole | Length: 5 cm | Length: 6.5 cm |
| Fruit | Weight: 412 g<br>Shape: Long oval but much more flat<br>Flesh: No fibers<br>Skin color: Green near 143B but will change as yellow near 9A when matured<br>Thickness of skin: 0.7–0.9 mm | Weight: 553.8 g<br>Shape: Long oval but much more round<br>Flesh: A little fibers<br>Skin color: Red near 45B or 70B on a green (149B) ground, but will change as red (45A) on a yellow (14B) ground<br>Thickness of skin: 0.8–1.0 mm |
| Core | Weight 35.6 g<br>Size: Axial diameter 151 mm; transverse diameter 37.6 mm | Weight: 43.8 g<br>Size: Axial diameter 142.6 mm; transverse diameter 40.3 mm<br>Core is easy to separate from the flesh like Irwin. |
| Seed | Weight: 17.3 g<br>Size: Axial diameter 76 mm; transverse diameter 28.2 mm | Weight: 21.3 g<br>Seed: Axial diameter 74.4 mm; transverse diameter 30.5 mm |
| Tree | Size: High | Size: Medium about 21 years old |
| Branch | Dense | Rare |
| Bark | Rough | Smooth |
| Vein | Same color with the leaf | Same color with the leaf but a little slice red (45B) in the early leafing about 7 days of each time |

| NAME | IRWIN |
|---|---|
| Leaf | Length: 26 cm<br>Width: 5.5 cm<br>Thickness: 0.5 cm<br>Color: Green near 141A |
| Petiole | Length: 6.5 cm |
| Fruit | Weight: 326 g<br>Shape: Oval as an egg<br>Flesh: A little fibers<br>Skin color: Purple red near 64A but will change as yellow gold near 15A<br>Thickness of skin: 0.93 mm–1.11 mm |
| Core | Weight: 48.3 g<br>Size: Axial diameter 104.8 mm; transverse diameter 39.8 mm. Core is easy to separate from the flesh. |
| Seed | Weight: 23.9 g<br>Size: Axial diameter 64.1 mm; transverse diameter 29.9 mm. |
| Tree | Size: Small |
| Branch | Dense more than FP1 |
| Bark | Smooth |
| Vein | Same as FP1 but near 143C |

Remarks: All color values expressed herein are those of the R.H.S. Color Chart

What is claimed is:

1. A new and distinct mango tree variety "FP1" as shown and described, as a result of hydrid cross of the cultivars "F1" and "Irwin" with more attractive fruit finish.

* * * * *